United States Patent
Joshi et al.

(10) Patent No.: US 7,449,696 B2
(45) Date of Patent: Nov. 11, 2008

(54) SYSTEM AND APPARATUS FOR HEAT MANAGEMENT

(75) Inventors: Ashutosh Joshi, Waukesha, WI (US); Joseph James Lacey, Cambridge, WI (US)

(73) Assignee: General Electric Company, Schenectady, NY (US)

(*) Notice: Subject to any disclaimer, the term of this patent is extended or adjusted under 35 U.S.C. 154(b) by 39 days.

(21) Appl. No.: 11/561,998

(22) Filed: Nov. 21, 2006

(65) Prior Publication Data

US 2008/0116388 A1  May 22, 2008

(51) Int. Cl.
 *G01T 1/24* (2006.01)
(52) U.S. Cl. .................. 250/370.15; 250/363.03; 250/363.05; 250/370.08; 62/513; 62/259.2; 378/19; 378/199
(58) Field of Classification Search ............... None
 See application file for complete search history.

(56) References Cited

U.S. PATENT DOCUMENTS

| | | | |
|---|---|---|---|
| 6,249,563 B1* | 6/2001 | Snyder et al. | 378/19 |
| 7,062,008 B2* | 6/2006 | Joshi et al. | 378/19 |
| 2004/0022351 A1* | 2/2004 | Lacey et al. | 378/19 |
| 2004/0071259 A1* | 4/2004 | Lacey et al. | 378/19 |
| 2005/0117698 A1* | 6/2005 | Lacey et al. | 378/19 |
| 2005/0287008 A1* | 12/2005 | Lacey et al. | 417/32 |

* cited by examiner

*Primary Examiner*—David P Porta
*Assistant Examiner*—Yara B Green
(74) *Attorney, Agent, or Firm*—Cantor Colburn LLP

(57) ABSTRACT

A heat management apparatus for disposition in a medical imaging system is disclosed. The apparatus includes a thermally conductive detector module, sensor components disposed upon the detector module, and signal processing electronics in thermal communication with the detector module, the signal processing electronics disposed proximate the sensor components. A main heat conductor is in thermal communication with a first defined portion of a length of the detector module, and a local heat conductor is in thermal communication with a second defined portion of the length of the detector module.

20 Claims, 2 Drawing Sheets

SYSTEM AND APPARATUS FOR HEAT MANAGEMENT

BACKGROUND OF THE INVENTION

The present disclosure relates generally to heat management, and particularly to heat management within imaging devices.

Current Computed Tomography (CT) systems use multi-slice detectors with data acquisition electronics that are connected to the detector modules. Although thermal stability of the detector module can influence image quality, the system is required to operate in a wide range of room temperature conditions. Current systems often use axial flow fans and flexible heaters to control the temperature of the detector module.

In order to improve the signal to noise ratio of the electronics, accommodate higher processing speeds, and reduce mechanical stresses on the rotating mass of the gantry, it is contemplated that future CT systems will include electronics that are disposed very close to the detector sensor (the scintillator and photodiode). This will pose additional engineering challenges to manage the heat generated by the electronics and control temperature variation throughout the detector.

Accordingly, there is a need in the art for a heat management arrangement that overcomes these drawbacks.

BRIEF DESCRIPTION OF THE INVENTION

An embodiment of the invention includes a heat management apparatus for disposition in a medical imaging system. The apparatus includes a thermally conductive detector module, sensor components disposed upon the detector module, and signal processing electronics in thermal communication with the detector module, the signal processing electronics disposed proximate the sensor components. A main heat conductor is in thermal communication with a first defined portion of a length of the detector module, and a local heat conductor is in thermal communication with a second defined portion of the length of the detector module.

Another embodiment of the invention includes a medical imaging system. The medical imaging system including a heat management apparatus, further including a thermally conductive detector module, sensor components disposed upon the detector module, and signal processing electronics in thermal communication with the detector module, the signal processing electronics disposed proximate the sensor components. A main heat conductor is in thermal communication with a first defined portion of a length of the detector module, and a local heat conductor is in thermal communication with a second defined portion of the length of the detector module.

BRIEF DESCRIPTION OF THE DRAWINGS

Referring to the exemplary drawings wherein like elements are numbered alike in the accompanying Figures.

DETAILED DESCRIPTION OF THE INVENTION

An embodiment of the invention provides an apparatus for heat management of contemplated CT detectors. In an embodiment, the detector is divided into multiple zones, and utilizes zonal, or local heat transfer members to conduct heat generated by the electronics away from the detector, thereby reducing a temperature gradient within the detector. In an embodiment, variable speed fans, in conjunction with heat exchangers, are configured to reduce detector temperature gradients in a wide range of room temperatures.

Figure 1:
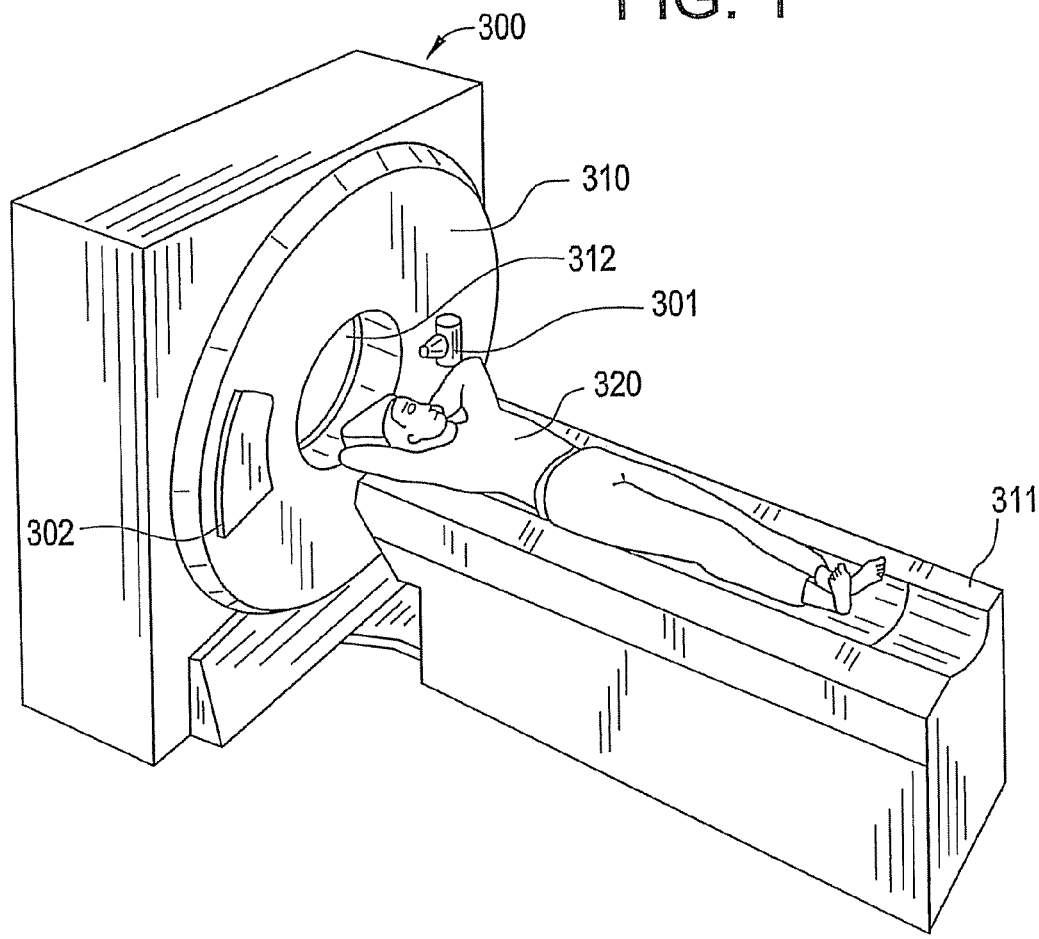
FIG. 1 depicts a top perspective view of a medical imaging system in accordance with an embodiment of the invention.
Figure 2:
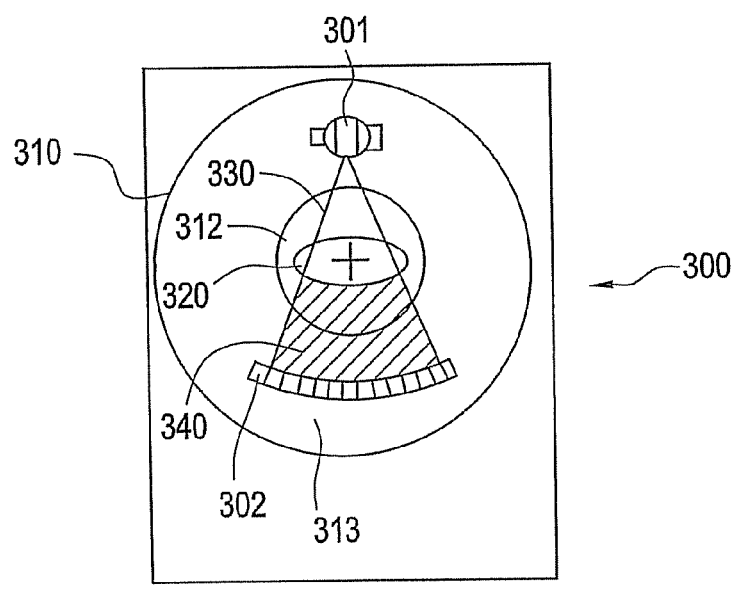
FIG. 2 depicts a schematic end view of a medical imaging system in accordance with an embodiment of the invention.

Referring now to FIG. 1 and FIG. 2, an exemplary CT imaging system 300 is depicted. The imaging system 300 includes a gantry 310 having a housing 313, an x-ray source 301, a radiation detector array 302, a patient support structure 311 and a patient cavity 312. The x-ray source 301 and the radiation detector array 302 are mounted within the housing 313, opposingly disposed so as to be separated by the patient cavity 312. In an exemplary embodiment, a patient 320 is disposed upon the patient support structure 311, which is then disposed within the patient cavity 312. The x-ray source 301 projects an x-ray beam 330 toward the radiation detector array 302 so as to pass through the patient 320. In an exemplary embodiment, the x-ray beam 330 is collimated by a collimator (not shown) so as to lie within an X-Y plane of a Cartesian coordinate system referred to as an "imaging plane". After passing through and becoming attenuated by the patient 320, the attenuated x-ray beam 340 is received by the radiation detector array 302. The radiation detector array 302 receives an attenuated x-ray beam 340 and produces an electrical signal responsive to the intensity of the attenuated x-ray beam 340.

X-ray projection data is obtained by rotating the gantry 310 around the patient 320 during a scan. The x-ray source 301 and the radiation detector array 302 are disposed within the housing 313, so as to allow the x-ray source 301 and the radiation detector array 302 to rotate with the gantry 310 around the patient support structure 311 when the patient support structure 311 is disposed within the patient cavity 312.

Figure 3:
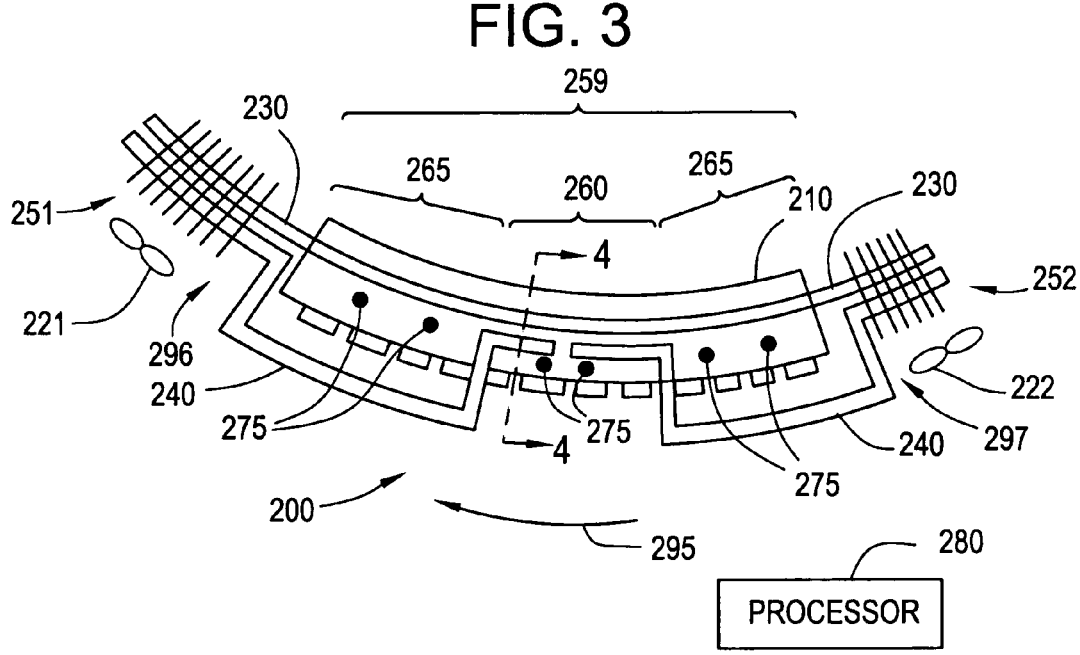
FIG. 3 depicts a schematic end view of a heat management system in accordance with an embodiment of the invention.
Figure 4:
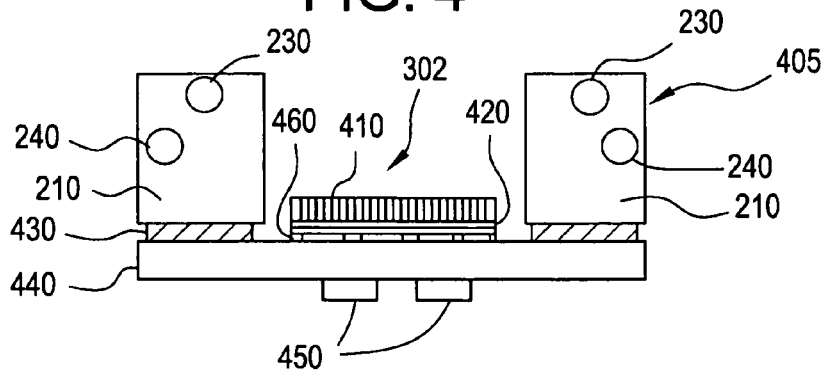
FIG. 4 depicts a schematic cross-section view of the heat management system of FIG. 3 in accordance with an embodiment of the invention.

Referring now to FIGS. 3 and 4, an exemplary embodiment of a heat management system, also herein referred to as a heat management apparatus, 200 is depicted. The heat management system 200 includes rails 210, a first and second flow enhancer 221, 222, main heat conductors 230, local heat conductors 240, also referred to as zonal heat conductors, and a first and second heat exchanger 251, 252. In an embodiment, the local heat conductors 240 have the same properties as the main heat conductors 230. The heat management system 200 also includes the detector array 302 including sensor components. In an embodiment as depicted in FIG. 4 the sensor components include a scintillator 410, and photodiodes 420. In an embodiment, the detector array 302 includes signal processing electronics. In an embodiment, the signal processing electronics include analog to digital (A/D) conversion circuits 460, and digital signal processing electronics, also herein referred to as digital electronics, 450, for example.

In an embodiment, the A/D circuits 460 and digital electronics 450 are disposed upon, and are in thermal communication with a thermally conductive detector module 405 proximate the sensor components. In an embodiment, the thermally conductive detector module 405 includes a substrate 440 and the rails 210. The rails 210 are disposed upon, and in thermal communication with the substrate 440. In an embodiment, the main heat conductors 230 and the local heat conductors 240 are in thermal communication with the rails 210. In an embodiment, the main heat conductors 230 and the local heat conductors 240 are disposed within the rails 210 as depicted. In an embodiment, the heat exchangers 251, 252 are in thermal communication with at least one of the main heat conductors 230 and the local heat conductors 240, and are configured to transfer heat from at least one of the main heat conductors 230 and the local heat conductors 240 to a cooling medium, such as air, for example. In an embodiment, the flow enhancers 221, 222, are configured to direct the cooling medium to the heat exchanger. It will be appreciated that in an embodiment, heat generated by the A/D circuits 460 and digital electronics 450 will be transferred to the cooling medium, as will be described further below. In an embodiment, the flow enhancers 221, 222 are fans.

While an embodiment of the invention has been described as part of a CT imaging system, it will be appreciated that the scope of the invention is not so limited, and that the invention will also apply to embodiments of other medical imaging systems, such as Radiography, Magnetic Resonance, and Positron Emission Tomography, for example. Further, while an embodiment of the invention has been depicted having one main heat conductor disposed within each rail, it will be appreciated that the scope of the invention is not so limited, and that the invention will also apply to heat management systems that may include other quantities of main heat conductor disposed within each rail, such as two, three, four, or more for example.

While an embodiment of the has been described using a fan as a flow enhancer, it will be appreciated that the scope of the invention is not so limited, and that the invention will also apply to heat management systems that have other flow enhancement devices to direct the cooling medium to the heat exchangers, such as a compressed air supply, diverters, and flow control nozzles, for example.

In an embodiment, the scintillator 410 is configured to emit a quantity of light in proportion to the attenuated x-ray beam 340 that it receives. The photodiodes 420 are configured to receive the emitted light, and to generate an analog electronic signal in proportion to the light emitted from the scintillator 410. In an embodiment, temperature differences, or gradients, within the detector 302 can have a negative influence on the performance of the scintillator 410 and photodiodes 420 of the detector array 302, and a thermo-mechanical integrity of the detector array 302, thereby compromising image quality.

The A/D circuits 460 are configured to convert the analog electrical signal into a digital signal. The digital electronics 450 are configured to receive and condition the digital signal converted by the A/D circuits 460. In an embodiment, the analog signals produced by the photodiodes 420 and the digital signals produced by the A/D circuits 460 are susceptible to transmission noise and interference. Accordingly, in an embodiment, to reduce the transmission distance, and therefore transmission noise and interference, between the photodiodes 420, the A/D circuits 460, and the digital electronics 450, the A/D circuits 460 are mounted on a same side of the substrate 440 as the photodiodes 420. Further, in an embodiment, the digital electronics 450 are disposed on the substrate 440 opposite the A/D circuits 460.

While an embodiment of the invention has described having a scintillator and photodiodes, it will be appreciated that the scope of the invention is not so limited, and that the invention will also apply to heat management systems that may have other image detection systems configured to be responsive to imaging energy, for example.

The A/D circuits 460 and the digital electronics 450 each consume power and generate heat in the process of converting and conditioning the digital signal. The heat generated by the A/D circuits 460 and the digital electronics 450 is transferred to the substrate 440, and then to the rails 210 through a thermal interface material 430 configured to reduce thermal resistance of the interface between the substrate 440 and the rails 210. In an embodiment, the rails 210 include Aluminum alloy configured to optimize heat transfer.

In an embodiment, the heat is then transferred from the rails 210 into the main heat conductors 230 and the local heat conductors 240. In an embodiment, the main heat conductor 230 and the local heat conductors 240 are highly thermally conductive heat pipes configured to be a super thermal conductor, that is, a device specifically selected because of a high thermal conductivity. The heat then flows through the heat conductors 230, 240 to the heat exchangers 251, 252. The heat exchangers 251, 252 are disposed at opposite ends of the length of the detector module 302, and are configured to remove heat from the heat conductors 230, 240, and to transfer the heat into the surrounding cooling medium. In an embodiment, the heat exchangers 251, 252 include fins to increase surface area and convective heat transfer capacity. In an embodiment, to further increase the heat transfer capacity, the flow enhancers 221, 222 are configured to direct the cooling medium to the heat exchangers 251, 252.

While an embodiment of the invention has been depicted having two heat exchangers, it will be appreciated that the scope of the invention is not so limited, and that the invention will also apply to heat management systems that may have other numbers of heat exchangers, such as one, three, four, or more, for example. Further, while an embodiment of the invention has been depicted with each heat exchanger in thermal communication with the main heat conductor and the local heat conductor, it will be appreciated that the scope of the invention is not so limited, and that the invention will also apply to heat management systems that may have heat exchangers in thermal communication with less than all of the heat conductors.

In an embodiment, the main heat conductor 230 is in thermal communication with a first defined portion 259 of the rails 210. In an embodiment, the heat conductors 230, 240 are bonded to the rails 210 using a thermally conductive epoxy to reduce the thermal resistance between the heat conductors 230, 240 and the rails 210, to effectively transfer the heat from rails 210 to the heat conductors 230, 240. In an embodiment, the first defined portion 259 of the rails 210 is defined to be an entire length of the rails 210, and includes a second defined portion 260, also herein referred to as a center region 260, as well as two edge regions 265. It will be appreciated that, in an embodiment, the first defined portion 259 is greater in length than the second defined portion 260. It will be appreciated that the main heat conductor 230 will remove heat from the first defined portion 259, or heat that is generated by the digital electronics 450 and the A/D circuits 460 disposed in the center region 260 of the detector 302, as well as heat generated by the digital electronics 450 and the A/D circuits 460 disposed in the edge regions 265. It will be further appreciated that the heat removed from the center region 260 must travel farther to reach the heat exchangers 251, 252 than the heat removed from the edge regions 265. Accordingly, the main heat conductor 230 will remove more heat from the edge regions 265 disposed proximate the heat exchangers 251, 252 than from the center region 260. It will be appreciated that, in an embodiment, removing more heat from the edge regions 265 will cause a temperature gradient along the length of the detector array 302 of the heat management system 200, wherein the temperature of the center region 260 of the rails 210 is greater than the temperature of the edge regions 265. As described above, the presence of the temperature gradient will have a negative impact on the performance of the detector array 302.

In an embodiment, the local heat conductors 240 are in thermal communication with the center region 260 of the rails 210. In an embodiment, the local heat conductors 240 are disposed and configured to remove the heat from the center region 260 generated by the digital electronics 450 and the A/D circuits 460. Accordingly, in an embodiment, the local heat conductors 240 are configured to cause a reduction in a magnitude of temperature gradient within, or along the length of, the rails 210 of the detector module 405.

While an embodiment of the invention has been depicted having one center and two edge regions with the local heat conductors in thermal communication with the center region, it will be appreciated that scope of the invention is not so limited, and that the invention will also apply to heat management systems that have more than one center and two edge regions, such as to have two, three, four, or more center regions with four, six, eight, or more edge regions. Further, while an embodiment of the invention has been depicted having only two local heat conductors, each in thermal communication with a single center region, it will be appreciated that the scope of the invention is not so limited, and that the invention will also apply to heat management systems that may have more than two local heat conductors in thermal communication with more than one region, such as two, three, four, or more regions, for example.

In an embodiment, the heat management system 200 further includes a processor 280. In an embodiment, the processor 280 is in signal communication with the flow enhancers 221, 222 and a set of temperature sensors 275 in thermal communication with the rails 210. In an embodiment, the set of temperature sensors 275 are disposed, distributed along the length, upon the surface of the rails 210. In an embodiment, the set of temperature sensors 275 are disposed, distributed along the length, within the material of the rails 210. In an embodiment, each temperature sensor 275 is responsive to a temperature of the detector module 405, and will generate a signal representative of the temperature at a location of the rail 210 at which the respective temperature sensor is disposed. In an embodiment, the processor 280 is configured to be receptive of the signals representative of the temperatures along the length of the rail 210, and thereby determine the magnitude of the temperature gradient within the rails 210.

In an embodiment, the first flow enhancer 221 is configured to direct the cooling medium to the first heat exchanger 251 and the second flow enhancer is configured to direct the cooling medium to the second heat exchanger 252. In an embodiment, the processor 280 is configured to generate, and make available to the flow enhancers 221, 222 a control signal responsive to the magnitude of the temperature gradient. In an embodiment, the processor 280 is responsive to the signal representative of temperature to make available a control signal to control the flow enhancers 221, 222 to cause a reduction in the magnitude of the temperature gradient within the detector module 405. In an embodiment, the flow enhancers 221, 222 are fans, and the processor 280 is configured to control the speed of the fans 221, 222 as necessary to reduce the temperature gradient along the length of the rails 210. That is, the processor 280 is configured to control the speed of the fans 221, 222 to maintain constant temperature along the length of the rails 210.

As described above, the detector 302 rotates with the gantry 310 around the patient support structure 311. In an embodiment, the heat management system 200 rotates in a direction indicated by reference numeral 295. Accordingly, there is a leading end 296, and a trailing end 297 opposite the leading end 296 relative to the length of the of the heat management system 200. During the rotation of the gantry 310, the leading end 296 and the trailing end 297 will be exposed to different air velocities and hence the fan 221, 222 speeds will be adjusted to balance the heat flow from the leading end 296 and the trailing end 297 to reduce the thermal gradient at the center 260 of the detector array 302 to enhance image quality of the CT system 300. In an embodiment, the processor 280 is responsive to motion of the detector module 405 to control the first flow enhancer 221 and the second flow enhancer 222 to reduce the magnitude of the temperature gradient within the detector module 405. In an embodiment, the processor 280 is responsive to motion of the detector module 405 to control the speed of the first fan 221 and the second fan 222 to reduce the magnitude of temperature gradient within the detector module 405.

Figure 5:
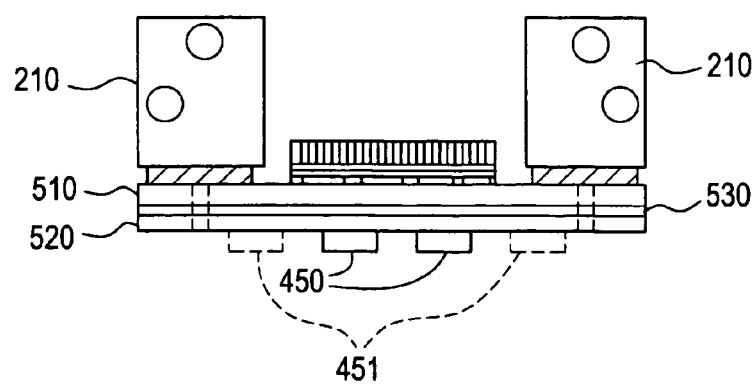
FIG. 5 depicts another schematic cross-section view of the heat management system of FIG. 3 in accordance with an embodiment of the invention.

Referring to FIG. 5, an embodiment of the invention is depicted having a top substrate 510 and a bottom substrate 520. In an embodiment, the top substrate 510 and the bottom substrate 520 are separated by a thermal distributor 530 to increase the distribution of heat generated by the A/D circuits 460 and the digital electronics 450 through the top substrate 510 and the bottom substrate 520. Increasing the heat distribution will thereby reduce a temperature gradient across the width of the heat management system 200, or between the two rails 210. In embodiment, the thermal distributor 530 is a graphite sheet. In an embodiment, the distribution of heat generated by the digital electronics 450 is increased, thereby reducing the temperature gradient across the width of the heat management system 200, by locating the digital electronics 450 closer to the rails 210, as depicted by reference numeral 451.

As disclosed, some embodiments of the invention may include some of the following advantages: the ability to improve imaging system signal to noise ratio; the ability to reduce mechanical stresses on the rotating mass of the gantry; the ability to increase image processing speeds; and the ability to reduce temperature gradients within the detector assembly and reduce thermo-mechanical stress on the detector parts.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A heat management apparatus configured for disposition in a medical imaging system, the apparatus comprising:
   a thermally conductive detector module having a thermally conductive rail;
   sensor components disposed upon the detector module;
   signal processing electronics disposed upon the detector module proximate the sensor components, the signal processing electronics in thermal communication with the rail;
   a main heat conductor in thermal communication with a first defined portion of a length of the rail; and
   a local heat conductor in thermal communication with a second defined portion of the length of the rail;
   wherein the second defined portion is a subset of the first defined portion, and the first defined portion is greater in length that the second defined portion;
   wherein the main heat conductor is disposed to conduct heat away from the first defined portion and the second defined portion, and the local heat conductor is disposed to conduct heat away from the second defined portion but not the first defined portion, thereby resulting in the second defined portion having a greater number of outgoing heat flow paths than does that portion of the first defined portion that does not include the second defined portion, thereby controlling the temperature gradient along the length of the rail.

2. The apparatus of claim 1, wherein:
   the detector module comprises a computed tomography detector module;
   the sensor components comprise a scintillator and a diode; and
   the signal processing electronics comprise Analog to Digital conversion circuits and digital signal processing circuits.

3. The apparatus of claim 1, wherein:
   the main heat conductor and the local heat conductor comprise heat transfer pipes.

4. The apparatus of claim 1, wherein:
   a magnitude of a temperature gradient within the detector module is increased in response to removal of heat from the first defined portion by the main heat conductor; and
   the magnitude of the temperature gradient within the detector module is reduced in response to removal of heat from the second defined portion by the local heat conductor.

5. The apparatus of claim 1, wherein:
   the first defined portion comprises an entire length of the detector module.

6. The apparatus of claim 1, further comprising:
   a heat exchanger in thermal communication with at least one of the main heat conductor and the local heat conductor;
   wherein the heat exchanger is configured to transfer heat from at least one of the main heat conductor and the local heat conductor to a cooling medium.

7. The apparatus of claim 6, further comprising:
   a flow enhancer to direct the cooling medium to the heat exchanger,
   a set of temperature sensors disposed proximate the detector module, the set of temperature sensors responsive to a temperature of the detector module; and
   a processor in signal communication with the set of temperature sensors and the flow enhancer, the processor responsive to a signal representative of temperature to make available to the flow enhancer a control signal;
   wherein the control signal shall cause a reduction in a magnitude of a temperature gradient within the detector module.

8. The apparatus of claim 7, wherein the heat exchanger is a first heat exchanger and the flow enhancer is a first flow enhancer, the apparatus further comprising:
   a second heat exchanger;
   wherein the first heat exchanger and the second heat exchanger are disposed at opposite ends of the length of the detector module;
   a second flow enhancer in signal communication with the processor to direct the cooling medium to the second heat exchanger;
   wherein the processor is responsive to motion of the detector module to control the first flow enhancer and the second flow enhancer to reduce the magnitude of the temperature gradient within the detector module.

9. The apparatus of claim 8, wherein:
   the first flow enhancer and the second flow enhancer are fans; and
   the processor is responsive to motion of the detector module to control the speed of the first fan and the speed of the second fan to reduce the magnitude of temperature gradient within the detector module.

10. The apparatus of claim 1, wherein the detector module comprises:
    a substrate upon which the sensor components and the signal processing electronics are disposed; and
    a rail in thermal communication with the substrate;
    wherein the main heat conductor and the local heat conductor are in thermal communication with the rail.

11. A medical imaging system comprising:
    a heat management apparatus comprising:
    a thermally conductive detector module having a thermally conductive rail;
    sensor components disposed upon the detector module;
    signal processing electronics disposed upon the detector module proximate the sensor components, the signal processing electronics in thermal communication with the rail;
    a main heat conductor in thermal communication with a first defined portion of a length of the rail; and
    a local heat conductor in thermal communication with a second defined portion of the length of the rail;
    wherein the second defined portion is a subset of the first defined portion, and the first defined portion is greater in length that the second defined portion;
    wherein the main heat conductor is disposed to conduct heat away from the first defined portion and the second defined portion, and the local heat conductor is disposed to conduct heat away from the second defined portion but not the first defined portion, thereby resulting in the second defined portion having a greater number of outgoing heat flow paths than does that portion of the first defined portion that does not include the second defined portion, thereby controlling the temperature gradient along the length of the rail.

12. The system of claim 11, wherein:
    the medical imaging system comprises a computed tomography medical imaging system;
    the detector module comprises a computed tomography detector module;
    the sensor components comprise a scintillator and a diode; and the signal processing electronics comprise Analog to Digital conversion circuits and digital signal processing circuits.

13. The system of claim 11, wherein:
a magnitude of a temperature gradient within the detector module is increased in response to removal of heat from the first defined portion by the main heat conductor; and
the magnitude of the temperature gradient within the detector module is reduced in response to removal of heat from the second defined portion by the local heat conductor.

14. The system of claim 11, wherein:
the first defined portion comprises an entire length of the detector module.

15. The system of claim 11, further comprising:
a heat exchanger in thermal communication with at least one of the main heat conductor and the local heat conductor;
wherein the heat exchanger is configured to transfer heat from at least one of the main heat conductor and the local heat conductor to a cooling medium.

16. The system of claim 15, further comprising:
a flow enhancer configured to direct the cooling medium to the heat exchanger; and
a set of temperature sensors disposed proximate the detector module, the set of temperature sensors responsive to a temperature of the detector module; and
a processor in signal communication with the set of temperature sensors and the flow enhancer, the processor responsive to a signal representative of temperature to make available to the flow enhancer a control signal;
wherein the control signal shall cause a reduction in a magnitude of a temperature gradient within the detector module.

17. The system of claim 16, wherein the heat exchanger is a first heat exchanger and the flow enhancer is a first flow enhancer, the apparatus further comprising:
a second heat exchanger;
wherein the first heat exchanger and the second heat exchanger are disposed at opposite ends of the length of the detector module; and
a second flow enhancer in signal communication with the processor to direct the cooling medium to the second heat exchanger;
wherein the processor is responsive to motion of the detector module to control the first flow enhancer and the second flow enhancer to reduce the magnitude of the temperature gradient within the detector module.

18. The system of claim 17, wherein:
the first flow enhancer and the second flow enhancer are fans; and
the processor is responsive to motion of the detector module to control the speed of the first fan and the speed of the second fan to reduce the magnitude of temperature gradient within the detector module.

19. The apparatus of claim 1, wherein:
the first defined portion includes two opposing outboard regions and an interdisposed central region;
the second defined portion includes the central region but not the two outboard regions;
the main heat conductor is disposed to conduct heat away from the central region and the two opposing outboard regions, and the local heat conductor is disposed to conduct heat away from the central region but not the two outboard regions, thereby resulting in the central region having a greater number of outgoing heat flow paths than do the two outboard regions for controlling the temperature gradient along the length of the rail.

20. The medical imaging system of claim 11, wherein:
the first defined portion includes two opposing outboard regions and an interdisposed central region;
the second defined portion includes the central region but not the two outboard regions;
the main heat conductor is disposed to conduct heat away from the central region and the two opposing outboard regions, and the local heat conductor is disposed to conduct heat away from the central region but not the two outboard regions, thereby resulting in the central region having a greater number of outgoing heat flow paths than do the two outboard regions for controlling the temperature gradient along the length of the rail.

* * * * *